(12) United States Patent
Kirsch et al.

(10) Patent No.: US 6,342,512 B1
(45) Date of Patent: Jan. 29, 2002

(54) SULFONYLCARBOXAMIDE DERIVATIVES, PROCESS FOR THEIR PREPARATION AND THEIR USE AS PHARMACEUTICALS

(75) Inventors: Reinhard Kirsch, Braunschweig; Hans-Ludwig Schaefer, Hochheim; Eugen Falk, Frankfurt; Horst Hemmerle, Bad Soden, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/654,841

(22) Filed: Sep. 1, 2000

(30) Foreign Application Priority Data

Sep. 1, 1999 (DE) .......................................... 199 41 540
Jun. 6, 2000 (DE) .......................................... 100 27 611

(51) Int. Cl.[7] ..................... C07D 211/14; C07D 401/10; C07D 401/14; A61K 31/4409
(52) U.S. Cl. ..................... 514/326; 514/331; 514/603; 514/604; 546/208; 546/234; 564/85; 564/86; 564/89; 564/90; 564/91; 564/92; 544/145; 544/357; 544/359
(58) Field of Search ................... 514/603, 604, 514/326, 331; 546/208, 234, 216; 564/86, 85, 89, 90, 91, 92; 544/145, 357, 359

(56) References Cited

U.S. PATENT DOCUMENTS 4,138,399 A    2/1979   Holland ................... 260/239.8

FOREIGN PATENT DOCUMENTS

DE    21 45 686    4/1972
DE    25 17 183    10/1976

OTHER PUBLICATIONS

Derwent Abstract of DE 25 17 183.
Derwent Abstract of DE 21 45 686.

*Primary Examiner*—Richard L. Raymond
*Assistant Examiner*—H Kahsay Habte
(74) *Attorney, Agent, or Firm*—Finnegan, Henderson, Farabow, Garrett & Dunner, LLP

(57) ABSTRACT

Sulfonylcarboxamide derivatives of formula I, their physiologically acceptable salts and/or physiologically functional derivatives, methods of making these compounds, their use for preparing medicines for the prevention and treatment of hyperlipidemia and arteriosclerotic disorders. The compounds of formula I have the following structure:

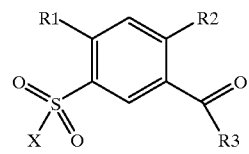

in which the radicals are as defined and their physiologically acceptable salts and physiologically functional derivatives are described.

12 Claims, No Drawings

SULFONYLCARBOXAMIDE DERIVATIVES, PROCESS FOR THEIR PREPARATION AND THEIR USE AS PHARMACEUTICALS

This application claims benefit under 35 U.S.C. §119 of application No. 19941540.4-44 filed on Sep. 1, 1999 and application No. 10027611.3 of Jun. 6, 2000 in Germany, which are hereby incorporated by reference.

The invention relates to sulfonylcarboxamide derivatives and their physiologically acceptable salts and physiologically functional derivatives and to their use for preparing medicines for the prevention and treatment of hyperlipidemia and arteriosclerotic disorders.

Sulfonylcarboxamides have already been described In Chemical Abstracts 96, 142393m (1982).

In DE 2145686, 2-chloro-5-sulfamylbenzoic acid derivatives have already been described as lipid-lowering agents.

The invention is based on the object of providing further compounds which have a therapeutically utilizable hypolipidemic action. In this context, the object was, in particular, also to provide compounds having an increased hypolipidemic action compared to the 2-chloro-5-sulfamylbenzoic acid derivatives from DE 2145686.

Accordingly, the invention relates to compounds of the formula I

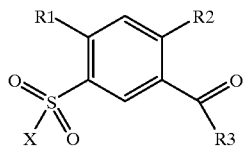

in which

X, R1, R2, R3 are, independently of one another, NR6R7, (CH$_2$)-pyridyl, (CH$_2$)$_n$-phenyl, where n can be 0–6 and the phenyl radical can be substituted up to two times by F, Cl, Br, CF$_3$, NH$_2$, CN, OCF$_3$, O—(C$_1$–C$_6$)-alkyl, S—(C$_1$–C$_6$)-alkyl, (C$_1$–C$_6$)-alkyl, (C$_3$–C$_6$)-cycloalkyl, COO(C$_1$–C$_6$)-alkyl, COO(C$_3$–C$_6$)-cycloalkyl, CONH$_2$, CONH(C$_1$–C$_6$)alkyl, CON[(C$_1$–C$_6$)alkyl]$_2$;

(C$_1$–C$_8$)-alkyl, pyrrolidinyl, piperidinyl, piperazinyl, 2-oxopiperazinyl, morpholinyl, tetrahydropyridinyl, tetrahydroquinolinyl, tetrahydroisoquinolinyl, it being possible for each of the rings to be substituted by phenyl, (C$_1$–C$_6$)-alkyl-phenyl, —OH, (C$_1$–C$_8$)-alkyl, (C$_1$–C$_6$)-alkyl-OH, O-phenyl, S-phenyl, (CO)—(C$_1$–C$_6$)-alkyl, (CO)-phenyl, where the phenyl substituent is unsubstituted or substituted up to two times by F, Cl, Br, OH, CF$_3$, CN, OCF$_3$, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, (C$_1$–C$_6$)-alkyl, (C$_3$–C$_6$)-cycloalkyl, COOH, COO(C$_1$–C$_6$)alkyl, COO(C$_3$–C$_6$)cycloalkyl, CONH$_2$, CONH(C$_1$–C$_6$)alkyl, CON[(C$_1$–C$_6$)alkyl]$_2$, CONH(C$_3$–C$_6$)cycloalkyl, NH$_2$, NH—CO—(C$_1$–C$_6$)-alkyl, NH—CO-phenyl;

R6 and R7 are, independently of one another, H, (C$_1$–C$_6$)-alkyl, (C$_1$–C$_6$)-alkyl—OH, (C$_1$–C$_6$)-alkyl-NH2, (C$_1$–C$_6$)-alkyl-O—(C$_1$–C$_6$)-alkyl, O—(C$_1$–C$_6$)-alkyl, (C$_3$–C$_6$)-cycloalkyl, CO—(C$_1$–C$_6$)-alkyl, (C$_1$–C$_6$)-alkyl-NH—C(O)—(C$_1$–C$_6$)-alkyl, (C$_1$–C$_6$)-alkyl-NH—(C$_1$–C$_6$)-alkyl, (C$_1$–C$_6$)-alkyl-N—[(C$_1$–C$_6$)-alkyl]$_2$, (C$_1$–C$_6$)-alkyl-di-phenyl, (C$_1$–C$_6$)-alkyl-O-phenyl, CHO, CO-phenyl, (CH$_2$)$_n$—Ar, where n can be 0–6, and Ar can be equal to phenyl, biphenylyl, 1- or 2-naphthyl, 1- or 2-tetrahydrofuranyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3-, 4- or 5-isoxazolyl, (C$_3$–C$_6$)-cycloalkyl, piperidinyl, pyrrolidinyl, oxopyridyl, 2- or 3-pyrrolyl, 2- or 3-pyridazinyl, 2-, 4- or 5-pyrimidinyl, 2-pyrazinyl, 2-(1,3,5-triazinyl), 2-, 3- or 4-morpholinyl, 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methylimidazol-2-, -4- or -5-yl and Ar can be substituted up to two times by F, Cl, Br, OH, CF$_3$, NO$_2$, CN, OCF$_3$, O—CH$_2$—O, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, (C$_1$–C$_6$)-alkyl, (C$_3$–C$_6$)-cycloalkyl, COOH, COO(C$_1$–C$_6$)alkyl, COO(C$_3$–C$_6$)cycloalkyl, CONH$_2$, CONH(C$_1$–C$_6$)alkyl, CON[(C$_1$–C$_6$)alkyl]$_2$, CONH(C$_3$–C$_6$)cycloalkyl, NH$_2$, NH—CO—(C$_1$–C$_6$)-alkyl, NH—CO-phenyl, pyrrolidin-1-yl, morpholin-1-yl, piperidin-1-yl, piperazin-1-yl, 4-methylpiperazin-1-yl, (CH$_2$)$_n$-phenyl, O—(CH$_2$)$_n$-phenyl, S—(CH$_2$)$_n$-phenyl, SO$_2$—(CH$_2$)$_n$-phenyl, where n=0–3;

and their physiologically acceptable salts.

Preference is given to compounds of the formula I in which one or more radical(s) is/are as defined below:

R1, R2 are, independently of one another, NR6R7, pyrrolidinyl, piperidinyl, piperazinyl, tetrahydropyridyl, it being possible for each of the rings to be substituted by phenyl, (C$_1$–C$_6$)-alkyl-phenyl, (C$_1$–C$_6$)-alkyl, (C$_1$–C$_6$)-alkyl-OH, O-phenyl, S-phenyl, (CO)—(C$_1$–C$_6$)-alkyl, (CO)-phenyl, where the phenyl substituent is unsubstituted or substituted up to two times by F, Cl, Br, CF$_3$, CN, OCF$_3$, O—(C$_1$–C$_6$)-alkyl, S-(C$_1$–C$_6$)-alkyl, (C$_1$–C$_6$)-alkyl, (C$_3$–C$_6$)-cycloalkyl, COOH, COO(C$_1$–C$_6$)-alkyl, COO(C$_3$–C$_6$)cycloalkyl, CONH$_2$, CONH(C$_1$–C$_6$)alkyl, CON[(C$_1$–C$_6$)alkyl]$_2$, NH$_2$, NH—CO—(C$_1$–C$_6$)-alkyl, NH—CO-phenyl;

R6, R7 are, independently of one another, H, (C$_1$–C$_6$)-alkyl, (C$_1$–C$_6$)-alkyl-O—(C$_1$–C$_6$)-alkyl, (C$_3$–C$_6$)-cycloalkyl, CO—(C$_1$–C$_6$)-alkyl, (C$_1$–C$_6$)-alkyl-NH—C(O)—(C$_1$–C$_6$)-alkyl, (C$_1$–C$_6$)-alkyl-NH—(C$_1$–C$_6$)-alkyl, (C$_1$–C$_6$)-alkyl-N—[(C$_1$–C$_6$)-alkyl]$_2$, (CH$_2$)$_n$—Ar, where n can be 0–6 and Ar can be equal to phenyl, biphenylyl, 1- or 2-naphthyl, 2-, 3- or 4-pyridyl, 2- or 3-thienyl, 2-, 4- or 5-thiazolyl, 2-, 4- or 5-oxazolyl, 3- or 5-isoxazolyl, (C$_3$–C$_6$)-cycloalkyl, piperidinyl, pyrrolidinyl, 2-, 4- or 5-pyrimidinyl, 2-, 3- or 4-morpholinyl, 2- or 5-benzimidazolyl, 2-benzothiazolyl or indol-3-yl, indol-5-yl and Ar can be substituted up to two times by F, Cl, Br, OH, CF$_3$, NO$_2$, CN, OCF$_3$, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, (C$_1$–C$_6$)-alkyl, (C$_3$–C$_6$)-cycloalkyl, COOH, COO(C$_1$–C$_6$)alkyl, COO(C$_3$–C$_6$)cycloalkyl, CONH$_2$, CONH(C$_1$–C$_6$) alkyl, NH$_2$, NH—CO-phenyl, (CH$_2$)$_n$-phenyl, O—(CH$_2$)$_n$-phenyl, S—(CH$_2$)$_n$-phenyl, where n=0–3;

X, R3 are, independently of one another, NR8R9, pyrrolidinyl, piperidinyl, morpholinyl, (C$_1$–C$_8$)-alkyl, (CH$_2$)$_n$-phenyl, where n=0–6 and the phenyl radical can be substituted up to two times by F, Cl, Br, CF$_3$, CN, OCF$_3$, O—(C$_1$–C$_6$)-alkyl, S—(C$_1$–C$_6$)-alkyl, (C$_1$–C$_6$)-alkyl, (C$_3$–C$_6$)-cycloalkyl, COO(C$_1$–C$_6$)-alkyl, COO(C$_3$–C$_6$)cycloalkyl, CONH$_2$, CONH(C$_1$–C$_6$)alkyl, CON[(C$_1$–C$_6$)alkyl]$_2$;

R8, R9 are, independently of one another, H, (C$_1$–C$_6$)-alkyl, (C$_3$–C$_6$)-cycloalkyl, CO—(C$_1$–C$_6$)-alkyl, (C$_1$–C$_6$)-alkyl-CO—(C$_1$–C$_6$)-alkyl, SO$_2$-benzyl, SO$_2$-benzyl-OCH$_3$, (CH$_2$)$_n$—Ar, where n can be 0–6 and Ar can be equal to phenyl or thienyl and Ar can be substituted up to two times by F, Cl, Br, CF$_3$, NO$_2$, CN, OCF$_3$, O—CH$_2$—O, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, (C$_1$–C$_6$)-alkyl, (C$_3$–C$_6$)-cycloalkyl, NH—CO-phenyl, (CH$_2$)$_n$-phenyl, O—(CH$_2$)$_n$-phenyl, S—(CH$_2$)$_n$-phenyl, SO$_2$—(CH$_2$)$_n$-phenyl, where n=0–2;

and their physiologically acceptable salts.

Particular preference is given to compounds of the formula I in which one or more radical(s) is/are as defined below:

R1, R2 are, independently of one another, NR6R7, piperidinyl, piperazinyl, tetrahydropyridyl, it being possible for each of the rings to be substituted by phenyl, (C$_1$–C$_6$)-alkyl-phenyl, (C$_1$–C$_6$)-alkyl, (CO)—(C$_1$–C$_6$)-alkyl;

R6, R7 are, independently of one another, H, (C$_1$–C$_6$)-alkyl, (C$_1$–C$_6$)-alkyl-NH—(C$_1$–C$_6$)-alkyl, (C$_1$–C$_6$)-alkyl-N—[(C$_1$–C$_6$)-alkyl]$_2$, (CH$_2$)$_n$—Ar, where n can be 0–6 and Ar can be equal to phenyl, 2-, 3- or 4-pyridyl, piperidinyl, pyrrolidinyl, 2-, 4- or 5-pyrimidinyl, 2-, 3- or 4-morpholinyl and Ar can be substituted up to two times by F, Cl, Br, OH, CF$_3$, NO$_2$, CN, OCF$_3$, O—(C$_1$–C$_6$)-alkyl, (C$_1$–C$_6$)-alkyl, COOH, NH$_2$,(CH$_2$)$_n$-phenyl, where n can be 0–3;

X is NR8R9, piperazinyl, (C$_1$–C$_6$)-alkyl, (CH$_2$)$_n$-phenyl, where n can be 0–6;

R3 is NR10R11, piperazinyl;

R8, R9 are, independently of one another, H, (C$_1$–C$_6$)-alkyl, (C$_3$–C$_6$)-cycloalkyl, CO—(C$_1$–C$_6$)-alkyl, (C$_1$–C$_6$)-alkyl-CO—(C$_1$–C$_6$)-alkyl, SO$_2$-benzyl, SO$_2$-benzyl-OCH$_3$, (CH$_2$)$_n$—Ar, where n can be 0–6 and Ar can be equal to phenyl or thienyl;

R10, R11 are, independently of one another, H, (C$_1$–C$_6$)-alkyl, (C$_3$–C$_6$)-cycloalkyl, CO—(C$_1$–C$_6$)-alkyl, (C$_1$–C$_6$)-alkyl-CO—(C$_1$–C$_6$)-alkyl, SO$_2$-benzyl, SO$_2$-benzyl-OCH$_3$, (CH$_2$)$_n$—Ar, where n can be 0–6 and Ar can be equal to phenyl or thienyl;

and their physiologically acceptable salts.

Very particular preference is given to compounds of the formula I in which one or more radical(s) is/are as defined below:

R1, R2 are, independently of one another, NR6R7, piperidinyl, piperazinyl, tetrahydropyridyl, it being possible for each of the rings to be substituted by phenyl, (C$_1$–C$_6$)-alkyl-phenyl, (C$_1$–C$_6$)-alkyl, (CO)—(C$_1$–C$_6$)-alkyl;

R6, R7 are, independently of one another, H, (C$_1$–C$_6$)-alkyl, (C$_1$–C$_6$)-alkyl-NH—(C$_1$–C$_6$)-alkyl, (C$_1$–C$_6$)-alkyl-N—[(C$_1$–C$_6$)-alkyl]$_2$, (CH$_2$)$_n$—Ar, where n can be 0–6 and Ar can be equal to phenyl, 2-, 3- or 4-pyridyl, piperidinyl, pyrrolidinyl, 2-, 4- or 5-pyrimidinyl, 2-, 3- or 4-morpholinyl and Ar can be substituted up to two times by F, Cl, Br, OH, CF$_3$, NO$_2$, CN, OCF$_3$, O—(C$_1$–C$_6$)-alkyl, (C$_1$–C$_6$)-alkyl, COOH, NH$_2$, (CH$_2$)$_n$-phenyl, where n can be 0–3;

X is (C$_1$–C$_6$)-alkyl, (CH$_2$)$_n$-phenyl, where n can be 0–6;

R3 is NR10R11, piperazinyl;

R10, R11 are, independently of one another, H, (C$_1$–C$_6$)-alkyl, (C$_3$–C$_6$)-cycloalkyl, CO—(C$_1$–C$_6$)-alkyl, (C$_1$–C$_6$)-alkyl-CO—(C$_1$–C$_6$)-alkyl, SO$_2$-benzyl, SO$_2$-benzyl-OCH$_3$, (CH$_2$)$_n$—Ar, where n can be 0–6 and Ar can be equal to phenyl or thienyl;

and their physiologically acceptable salts.

The invention relates to compounds of the formula I in the form of their racemates, racemic mixtures and pure enantiomers, and to their diastereomers and mixtures thereof. The alkyl, alkenyl and alkynyl radicals in the substituents X, R1, R2, R3, R6, R7, R8, R10 and R11 may be either straight-chain or branched.

Pharmaceutically acceptable salts are particularly suitable for medical applications because their solubility in water is higher than that of the initial or basic compounds. These salts must have a pharmaceutically acceptable anion or cation. Suitable pharmaceutically acceptable acid addition salts of compounds of the formula I are salts of inorganic acids such as hydrochloric, hydrobromic, phosphoric, metaphosphoric, nitric, sulfonic and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise fall within the scope of the invention as useful intermediates for preparing or purifying pharmaceutically acceptable salts and/or for use in nontherapeutic, for example in vitro, applications.

Preference is given to the salts of methanesulfonic acid, toluenesulfonic acid, maleic acid and phosphoric acid.

Particular preference is given to the methanesulfonates of the compounds of the formula I.

The invention furthermore relates to physiologically functional derivatives of the compounds of the formula I. The term "physiologically functional derivative" used herein refers to any physiologically tolerated derivative of a compound according to the invention, for example an ester, which is able on administration to a mammal, such as, for example, a human, to form (directly or indirectly) such a compound or an active metabolite thereof.

A further aspect of this invention is the use of prodrugs of the compounds of the formula I. Such prodrugs can be metabolized in vivo to a compound of the formula I. These prodrugs may themselves be active or not.

The compounds of the formula I may also exist in various polymorphous forms, for example as amorphous and crystalline polymorphous forms. All polymorphous forms of the compounds of the formula I lie within the scope of the invention and are a further aspect of the invention.

All references hereinafter to "compound(s) of formula (I)" refer to compound(s) of the formula (I) as described above, and the salts, solvates and physiologically functional derivatives thereof as described herein.

The amount of a compound of formula (I) which is necessary to achieve the desired biological effect depends on a number of factors, for example the specific compound chosen, the intended use, the mode of administration and the clinical condition of the patient. In general, the daily dose is in the range from 0.3 mg to 100 mg (typically from 3 mg to 50 mg) per day and per kilogram of body weight, for example 3–10 mg/kg/day. An intravenous dose may be, for example, in the range from 0.3 mg to 1.0 mg/kg, which can most suitably be administered as infusion of from 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. It is thus possible for ampoules for injections to contain, for example, from 1 mg to 100 mg, and single-dose formulations which can be administered orally, such as, for example, tablets or capsules, to contain, for example, from 1.0 to 1000 mg, typically from 10 to 600 mg. In the case of pharmaceutically acceptable salts, the aforementioned weight data are based on the weight of the salt of the compound of the formula (I). For the prophylaxis or therapy of the abovementioned conditions, the compounds of formula (I) themselves can be used as the compound, but they are preferably in the form of a pharmaceutical composition with an acceptable carrier. The carrier must, of course, be acceptable in the sense that it is compatible with the other ingredients of the composition and is not hazardous for the patient's health. The carrier may be a solid or a liquid or both and is preferably formulated with the compound as a single dose, for example as a tablet which may contain from 0.05% to 95% by weight of the active ingredient. Further pharmaceutically active substances may likewise be present, including other compounds of formula (I). The pharmaceutical compositions according to the invention can be produced by one of the known pharmaceutical methods which essentially consist in mixing the ingredients with pharmacologically acceptable carriers and/or excipients.

Pharmaceutical compositions according to the invention are those suitable for oral, rectal, topical, peroral (for example sublingual) and parenteral (for example subcutaneous, intramuscular, intradermal or intravenous) administration although the most suitable mode of administration in each individual case depends on the nature and severity of the condition to be treated and on the nature of the compound of formula (I) used in each case. Coated formulations and coated slow-release formulations also lie within the scope of the invention. Formulations resistant to acid and gastric fluid are preferred. Suitable coatings resistant to gastric fluid comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, lozenges or tablets, each of which contain a defined amount of the compound of formula (I); as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tabletting the compound in free-flowing form, such as, for example, a powder or granules, where appropriate mixed with a binder, lubricant, inert diluent and/or a (plurality of) surface-active/dispersing agent(s) in a suitable machine. Molded tablets can be produced by molding the compound which is in powder form and is moistened with an inert liquid diluent in a suitable machine.

Pharmaceutical compositions suitable for peroral (sublingual) administration comprise lozenges which contain a compound of formula (I) with a flavoring, normally sucrose and gum arabic or tragacanth, and pastilles which comprise the compound in an inert base such as gelatin and glycerol or sucrose and gum arabric.

Suitable pharmaceutical compositions for parenteral administration preferably comprise sterile aqueous preparations of a compound of formula (I), which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions according to the invention generally contain from 0.1 to 5% by weight of the active compound.

Suitable pharmaceutical compositions for rectal administration are preferably in the form of single-dose suppositories. These can be produced by mixing a compound of formula (I) with one or more conventional solid carriers, for example cocoa butter, and shaping the resulting mixture.

Suitable pharmaceutical compositions for topical application to the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%. Transdermal administration is also possible. Suitable pharmaceutical compositions for transdermal uses can be in the form of single plasters which are suitable for long-term close contact with the patient's epidermis. Such plasters suitably contain the active ingredient in an optionally buffered aqueous solution, dissolved and/or dispersed in an adhesive or dispersed in a polymer. A suitable active ingredient concentration is about 1% to 35%, preferably about 3% to 15%. As a particular possibility, the active ingredient can be released as described, for example, in Pharmaceutical Research, 2(6): 318 (1986) by electrotransport or iontophoresis.

The following preparations serve to illustrate the invention without restricting it, however.

EXAMPLE A

Soft gelatin capsules containing 100 mg of active ingredient per capsule:

|  | per capsule |
|---|---|
| Active ingredient | 100 mg |
| Triglyceride mixture fractionated from coconut fat | 400 mg |
| Capsule contents | 500 mg |

EXAMPLE B
Emulsion containing 60 mg of active ingredient per 5 ml:

|  | per 100 ml emulsion |
|---|---|
| Active ingredient | 1.2 g |
| Neutral oil | q.s. |
| Sodium carboxymethylcellulose | 0.6 g |
| Polyoxyethylene stearate | q.s. |
| Glycerol, pure | 0.2 to 2.0 g |
| Flavoring | q.s. |
| Water (deionized or distilled) | ad 100 ml |

EXAMPLE C
Rectal pharmaceutical form containing 40 mg of active ingredient per suppository:

|  | per suppository |
|---|---|
| Active ingredient | 40 mg |
| Suppository base | ad 2 g |

EXAMPLE D
Tablets containing 40 mg of active ingredient per tablet:

|  | per tablet |
|---|---|
| Active ingredient | 40 mg |
| Lactose | 600 mg |
| Corn starch | 300 mg |
| Soluble starch | 20 mg |
| Magnesium stearate | 40 mg |
|  | 1000 mg |

EXAMPLE E
Coated tablets containing 50 mg of active ingredient per coated tablet:

|  | per coated tablet |
|---|---|
| Active ingredient | 50 mg |
| Corn starch | 100 mg |
| Lactose | 60 mg |
| Sec. calcium phosphate | 30 mg |
| Soluble starch | 5 mg |
| Magnesium stearate | 10 mg |
| Colloidal silica | 5 mg |
|  | 260 mg |

EXAMPLE F
The following formulas are suitable for producing the contents of hard gelatin capsules:

| a) | Active ingredient | 100 mg |
|---|---|---|
|  | Corn starch | 300 mg |
|  |  | 400 mg |

| b) | Active ingredient | 140 mg |
|---|---|---|
|  | Lactose | 180 mg |
|  | Corn starch | 180 mg |
|  |  | 500 mg |

EXAMPLE G

Drops can be produced in accordance with the following formula (100 mg of active ingredient in 1 ml = 20 drops):

| Active ingredient | 10 g |
|---|---|
| Methyl benzoate | 0.07 g |
| Ethyl benzoate | 0.03 g |
| Ethanol 96% pure | 5 ml |
| Demineralized water | ad 100 ml |

The invention also relates to a process for preparing the compounds of the formula I, which comprises preparing compounds of the formula I as shown in the following reaction diagram:

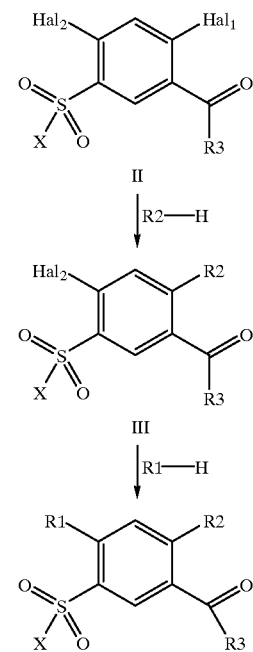

The examples detailed below serve to illustrate the invention without restricting it, however. The stated decomposition points are not corrected and generally depend on the heating rate.

TABLE 1

Examples

Formula I

| Ex. | R1 | R2 | R3 | X | Empirical formula | Molecular mass | MS (M + H⁺) |
|---|---|---|---|---|---|---|---|
| 1 | NH-ethyl-pyrrolidinyl | piperazin-1-yl-4-CH₃ | N(CH₃)-phenyl | N(CH₃)-phenyl | C32 H42 N6 O3 S | 590.8 | 591.3 |
| 2 | NH-propyl-phenyl | piperazin-1-yl-4-CH₃ | N(CH₃)-phenyl | N(CH₃)-phenyl | C35 H41 N5 O3 S | 611.8 | 612.4 |
| 3 | NH-ethyl-phenyl | piperazin-1-yl-4-CH₃ | N(CH₃)-phenyl | N(CH₃)-phenyl | C34 H39 N5 O3 S | 597.8 | 598.4 |
| 4 | NH-piperidin-4-yl-1-benzyl | piperazin-1-yl-4-CH₃ | N(CH₃)-phenyl | N(CH₃)-phenyl | C38 H46 N6 O3 S | 666.9 | 667.4 |
| 5 | NH—CH₂-pyrid-2-yl | piperazin-1-yl-4-CH₃ | N(CH₃)-phenyl | N(CH₃)-phenyl | C32 H36 N6 O3 S | 584.7 | 585.3 |
| 6 | NH-ethyl-morpholin-4-yl | piperazin-1-yl-4-CH₃ | N(CH₃)-phenyl | N(CH₃)-phenyl | C32 H42 N6 O4 S | 606.8 | 607.4 |
| 7 | piperazin-1-yl-4-phenyl | piperazin-1-yl-4-CH₃ | N(CH₃)-phenyl | N(CH₃)-phenyl | C36 H42 N6 O3 S | 638.8 | 639.3 |
| 8 | NH-4-t-butyl-benzyl | piperazin-1-yl-4-CH₃ | N(CH₃)-phenyl | N(CH₃)-phenyl | C37 H45 N5 O3 S | 639.9 | 640.3 |
| 9 | piperidin-1-yl-4-benzyl | piperazin-1-yl-4-CH₃ | N(CH₃)-phenyl | N(CH₃)-phenyl | C38 H45 N5 O3 S | 651.9 | 652.3 |
| 10 | piperidin-1-yl-4-phenyl | piperazin-1-yl-4-CH₃ | N(CH₃)-phenyl | N(CH₃)-phenyl | C37 H43 N5 O3 S | 637.8 | 638.3 |
| 11 | piperazin-1-yl-4-acetyl | piperazin-1-yl-4-CH₃ | N(CH₃)-phenyl | N(CH₃)-phenyl | C32 H40 N6 O4 S | 604.8 | 605.4 |
| 12 | N(ethyl)-ethyl-N(CH₃)₂ | piperazin-1-yl-4-CH₃ | N(CH₃)-phenyl | N(CH₃)-phenyl | C32 H44 N6 O3 S | 592.8 | 593.4 |
| 13 | NH-ethyl-phenyl | piperazin-1-yl-4-CH₃ | N(CH₃)-phenyl | CH₃ | C28 H34 N4 O3 S | 506.7 | 507.2 |
| 14 | NH-piperidin-4-yl-1-benzyl | piperazin-1-yl-4-CH₃ | N(CH₃)-phenyl | CH₃ | C32 H41 N5 O3 S | 575.8 | 576.3 |
| 15 | NH-ethyl-phenyl | piperazin-1-yl-4-CH₃ | N(ethyl)₂ | CH₂-phenyl | C31 H40 N4 O3 S | 548.7 | 549.3 |
| 16 | NH-piperidin-4-yl-1-benzyl | piperazin-1-yl-4-CH₃ | N(ethyl)₂ | CH₂-phenyl | C35 H47 N5 O3 S | 617.9 | 618.4 |
| 17 | NH-ethyl-N-pyrrolidinyl | NH-piperidin-4-yl-1-benzyl | N(CH₃)-phenyl | N(CH₃)-phenyl | C39 H47 N5 O3 S | 665.9 | 666.3 |
| 18 | NH-ethyl-N-pyrrolidinyl | NH—CH₂-pyrid-2-yl | N(CH₃)-phenyl | N(CH₃)-phenyl | C33 H38 N6 O3 S | 598.8 | 599.3 |
| 19 | NH-ethyl-N-pyrrolidinyl | NH-ethyl-phenyl | N(CH₃)-phenyl | N(CH₃)-phenyl | C35 H41 N5 O3 S | 611.8 | 612.3 |
| 20 | NH-ethyl-N-pyrrolidinyl | piperidin-1-yl-4-phenyl | N(CH₃)-phenyl | N(CH₃)-phenyl | C38 H45 N5 O3 S | 651.9 | 652.3 |
| 21 | NH-ethyl-N-pyrrolidinyl | piperazin-1-yl-4-phenyl | N(CH₃)-phenyl | N(CH₃)-phenyl | C37 H44 N6 O3 S | 652.9 | 653.3 |
| 22 | piperidin-1-yl-4-benzyl | NH-ethyl-N-pyrrolidinyl | N(CH₃)-phenyl | N(CH₃)-phenyl | C39 H47 N5 O3 S | 665.9 | 666.3 |
| 23 | NH—CH₂-pyrid-2-yl | NH-ethyl-N-pyrrolidinyl | N(CH₃)-phenyl | N(CH₃)-phenyl | C33 H38 N6 O3 S | 598.8 | 599.3 |
| 24 | NH-ethyl-phenyl | NH-ethyl-N-pyrrolidinyl | N(CH₃)-phenyl | N(CH₃)-phenyl | C35 H41 N5 O3 S | 611.8 | 612.3 |
| 25 | piperidin-1-yl-4-phenyl | NH-ethyl-N-pyrrolidinyl | N(CH₃)-phenyl | N(CH₃)-phenyl | C38 H45 N5 O3 S | 651.9 | 652.3 |
| 26 | piperazin-1-yl-4-phenyl | NH-ethyl-N-pyrrolidinyl | N(CH₃)-phenyl | N(CH₃)-phenyl | C37 H44 N6 O3 S | 652.9 | 653.4 |
| 27 | NH-piperidin-4-yl-1-benzyl | piperazin-1-yl-4-CH₃ | piperidin-1-yl | CH₃ | C30 H43 N5 O3 S | 553.8 | 554.3 |
| 28 | piperazin-1-yl-4-phenyl | piperazin-1-yl-4-CH₃ | piperidin-1-yl | CH₃ | C28 H39 N5 O3 S | 525.7 | 526.3 |
| 29 | NH-butyl-phenyl | piperazin-1-yl-4-CH₃ | piperidin-1-yl | CH₃ | C28 H40 N4 O3 S | 512.7 | 513.3 |
| 30 | piperidin-1-yl-4-benzyl | piperazin-1-yl-4-CH₃ | piperidin-1-yl | CH₃ | C30 H42 N4 O3 S | 538.8 | 539.3 |
| 31 | NH—CH₂-pyrid-2-yl | piperazin-1-yl-4-CH₃ | N(ethyl)₂ | CH₂-phenyl | C29 H37 N5 O3 S | 535.7 | 536.3 |
| 32 | piperazin-1-yl-4-phenyl | N(ethyl)-ethyl-N(CH₃)₂ | N(ethyl)₂ | CH₂-phenyl | C34 H47 N5 O3 S | 605.8 | 606.3 |
| 33 | piperazin-1-yl-4-phenyl | piperazin-1-yl-4-CH₃ | NH-propyl-OCH₃ | CH₃ | C27 H39 N5 O4 S | 529.7 | 530.3 |
| 34 | piperidin-1-yl-4-phenyl | piperazin-1-yl-4-CH₃ | NH-propyl-OCH₃ | CH₃ | C28 H40 N4 O4 S | 528.7 | 529.3 |
| 35 | piperidin-1-yl-4-benzyl | piperazin-1-yl-4-CH₃ | NH-propyl-OCH₃ | CH₃ | C29 H42 N4 O4 S | 542.7 | 543.3 |
| 36 | NH-piperidin-4-yl | piperazin-4-yl-2-on | N(CH₃)-phenyl | N(CH₃)-phenyl | C30 H36 N6 O4 S | 576.7 | 577.4 |
| 37 | piperidin-1-yl-4-phenyl | piperazin-1-yl-4-CH₃ | piperidin-1-yl | piperidin-1-yl | C33 H47 N5 O3 S | 593.8 | 594.3 |
| 38 | NH-ethyl-phenyl | piperazin-1-yl-4-CH₃ | piperidin-1-yl | piperidin-1-yl | C30 H43 N5 O3 S | 553.8 | 554.3 |
| 39 | NH-piperidin-4-yl-1-benzyl | piperazin-1-yl-4-CH₃ | piperidin-1-yl | piperidin-1-yl | C34 H49 N5 O3 S | 607.9 | 608.4 |
| 40 | piperidin-1-yl-4-phenyl | piperazin-1-yl-4-CH₃ | NH—CH₂-thien-2-yl | NH—CH₂-thien-2-yl | C33 H39 N5 O3 S3 | 649.9 | 650.2 |
| 41 | NH-butyl-phenyl | piperazin-1-yl-4-CH₃ | NH—CH₂-thien-2-yl | NH—CH₂-thien-2-yl | C32 H39 N5 O3 S3 | 637.9 | 638.2 |
| 42 | piperidin-1-yl-4-phenyl | N(ethyl)-ethyl-N(CH₃)₂ | N(ethyl)₂ | benzyl | C35 H48 N4 O3 S | 604.9 | 605.3 |
| 43 | NH-propyl-phenyl | piperazin-1-yl-4-CH₃ | N(CH₃)-phenyl | N(CH₃)-phenyl | C35 H41 N5 O3 S | 611.8 | 612.3 |
| 44 | NH-benzyl | piperazin-1-yl-4-CH₃ | N(CH₃)-phenyl | N(CH₃)-phenyl | C33 H37 N5 O3 S | 583.8 | 584.2 |
| 45 | NH-(p-CF₃O-benzyl) | piperazin-1-yl-4-CH₃ | N(CH₃)-phenyl | N(CH₃)-phenyl | C34 H36 F3 N5 O4 S | 667.7 | 668.2 |
| 46 | 1,2,5,6-tetrahydropyrid-1-yl-4-phenyl | piperazin-1-yl-4-CH₃ | NH-propyl-OCH₃ | CH₃ | C28 H38 N4 O4 S | 526.7 | 527.3 |
| 47 | 1,2,5,6-tetrahydropyrid-1-yl-4-phenyl | piperazin-1-yl-4-CH₃ | piperidin-1-yl | CH₃ | C29 H38 N4 O3 S | 522.7 | 523.3 |
| 48 | 1,2,5,6-tetrahydropyrid-1-yl-4-phenyl | piperazin-1-yl-4-CH₃ | NH—CH₂-thien-2-yl | NH—CH₂-thien-2-yl | C33 H37 N5 O3 S3 | 647.9 | 648.1 |
| 49 | piperidin-1-yl-4-phenyl | piperazin-1-yl-4-CH₃ | NH—C₂H₄-thien-2-yl | NH—C₂H₄-thien-2-yl | C35 H43 N5 O3 S3 | 678.0 | 678.3 |
| 50 | NH-phenethyl | piperazin-1-yl-4-CH₃ | NH—C₂H₄-thien-2-yl | NH—C₂H₄-thien-2-yl | C32 H39 N5 O3 S3 | 637.9 | 638.2 |
| 51 | NH-piperidin-4-yl-1-benzyl | piperazin-1-yl-4-CH₃ | NH—C₂H₄-thien-2-yl | NH—C₂H₄-thien-2-yl | C36 H46 N6 O3 S3 | 707.0 | 707.2 |
| 52 | piperazin-1-yl-4-phenyl | piperazin-1-yl-4-CH₃ | NH—C₂H₄-thien-2-yl | NH—C₂H₄-thien-2-yl | C34 H42 N6 O3 S3 | 678.9 | 679.2 |

TABLE 1-continued

Examples

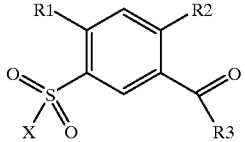

Formula I

| Ex. | R1 | R2 | R3 | X | Empirical formula | Molecular mass | MS (M + H$^+$) |
|---|---|---|---|---|---|---|---|
| 53 | piperidin-1-yl-4-benzyl | NH-ethyl-N-pyrrolidinyl | NH-pentyl | CH$_3$ | C31 H46 N4 O3 S | 554.8 | 555.4 |
| 54 | piperidin-1-yl-4-phenyl | NH-ethyl-N-pyrrolidinyl | NH-pentyl | CH$_3$ | C30 H44 N4 O3 S | 540.8 | 541.4 |
| 55 | 1,2,5,6-tetrahydropyrid-1-yl-4-phenyl | NH-ethyl-N-pyrrolidinyl | NH-pentyl | CH$_3$ | C30 H42 N4 O3 S | 538.8 | 539.3 |
| 56 | piperidin-1-yl-4-benzyl | piperazin-1-yl-4-CH$_3$ | Piperidin-1-yl | CH$_3$ | C30 H42 N4 O3 S | 538.8 | 539.3 |
| 57 | piperidin-1-yl-4-benzyl | NH-ethyl-N-pyrrolidinyl | NH-propyl-OCH$_3$ | CH$_3$ | C30 H44 N4 O4 S | 556.8 | 557.4 |
| 58 | piperidin-1-yl-4-phenyl | NH-ethyl-N-pyrrolidinyl | NH-propyl-OCH$_3$ | CH$_3$ | C29 H42 N4 O4 S | 542.7 | 543.4 |
| 59 | 1,2,5,6-tetrahydropyrid-1-yl-4-phenyl | NH-ethyl-N-pyrrolidinyl | NH-propyl-OCH$_3$ | CH$_3$ | C29 H40 N4 O4 S | 540.7 | 541.4 |
| 60 | NH-piperidin-4-yl-1-benzyl | NH-ethyl-N-pyrrolidinyl | NH-propyl-OCH$_3$ | CH$_3$ | C30 H45 N5 O4 S | 571.8 | 572.4 |
| 61 | piperidin-1-yl-4-phenyl | —N(acetyl)-ethyl-N-pyrrolidinyl | NH-propyl-OCH$_3$ | CH$_3$ | C31 H44 N4 O5 S | 584.8 | 585.3 |
| 62 | piperidin-1-yl-4-benzyl | N(methyl)-ethyl-N(CH$_3$)$_2$ | NH-propyl-OCH$_3$ | CH$_3$ | C29 H44 N4 O4 S | 544.8 | 545.3 |
| 63 | piperidin-1-yl-4-phenyl | N(methyl)-ethyl-N(CH$_3$)$_2$ | NH-propyl-OCH$_3$ | CH$_3$ | C28 H42 N4 O4 S | 530.7 | 531.4 |
| 64 | 1,2,5,6-tetrahydropyrid-1-yl-4-phenyl | N(methyl)-ethyl-N(CH$_3$)$_2$ | NH-propyl-OCH$_3$ | CH$_3$ | C28 H40 N4 O4 S | 528.7 | 529.3 |
| 65 | NH-piperidin-4-yl-1-benzyl | N(methyl)-ethyl-N(CH$_3$)$_2$ | NH-propyl-OCH$_3$ | CH$_3$ | C29 H45 N5 O4 S | 559.8 | 560.4 |
| 66 | piperidin-1-yl-4-phenyl | N(methyl)-ethyl-N(CH$_3$)$_2$ | piperidin-1-yl | CH$_3$ | C29 H42 N4 O3 S | 526.7 | 527.4 |
| 67 | piperidin-1-yl-4-benzyl | N(methyl)-ethyl-N(CH$_3$)$_2$ | piperidin-1-yl | CH$_3$ | C30 H44 N4 O3 S | 540.8 | 541.4 |
| 68 | piperidin-1-yl-4-benzyl | NH-ethyl-N-pyrrolidinyl | piperidin-1-yl | CH$_3$ | C31 H44 N4 O3 S | 552.8 | 553.4 |
| 69 | NH-piperidin-4-yl-1-benzyl | NH-ethyl-N-pyrrolidinyl | piperidin-1-yl | CH$_3$ | C31 H45 N5 O3 S | 567.8 | 568.4 |
| 70 | piperidin-1-yl-4-phenyl | NH-ethyl-N-pyrrolidinyl | N(ethyl)$_2$ | benzyl | C35 H46 N4 O3 S | 602.8 | 603.4 |
| 71 | piperidin-1-yl-4-phenyl | N(ethyl)-ethyl-N(CH$_3$)$_2$ | N(ethyl)$_2$ | benzyl-3-OCH$_3$ | C36 H50 N4 O4 S | 634.9 | 635.4 |
| 72 | piperidin-1-yl-4-phenyl | N(ethyl)-ethyl-N(CH$_3$)$_2$ | N(ethyl)$_2$ | benzyl | C36 H50 N4 O3 S | 618.9 | 619.4 |
| 73 | piperidin-1-yl-4-(p-F-phenyl) | NH-ethyl-N-pyrrolidinyl | NH-pentyl | benzyl | C36 H47 F N4 O3 S | 634.9 | 635.2 |
| 74 | piperidin-1-yl-4-(p-OCH$_3$-phenyl) | NH-ethyl-N-pyrrolidinyl | NH-pentyl | benzyl | C37 H50 N4 O4 S | 646.9 | 647.2 |
| 75 | piperidin-1-yl-4-(p-CH$_3$-phenyl) | NH-ethyl-N-pyrrolidinyl | NH-pentyl | benzyl | C37 H50 N4 O3 S | 630.9 | 631.2 |
| 76 | piperidin-1-yl-4-(p-F-phenyl) | N(ethyl)-ethyl-N(CH$_3$)$_2$ | NH-pentyl | benzyl | C36 H49 F N4 O3 S | 636.9 | 637.2 |
| 77 | piperidin-1-yl-4-(p-OCH$_3$-phenyl) | N(ethyl)-ethyl-N(CH$_3$)$_2$ | NH-pentyl | benzyl | C37 H52 N4 O4 S | 648.9 | 649.3 |
| 78 | piperidin-1-yl-4-(p-CH$_3$-phenyl) | N(ethyl)-ethyl-N(CH$_3$)$_2$ | NH-pentyl | benzyl | C37 H52 N4 O3 S | 632.9 | 633.3 |
| 79 | piperidin-1-yl-4-hydroxy | NH-ethyl-N-pyrrolidinyl | NH-pentyl | benzyl | C30 H44 N4 O4 S | 556.9 | 557.4 |
| 80 | piperidin-1-yl-4-phenoxy | N(ethyl)-ethyl-N(CH$_3$)$_2$ | NH-pentyl | benzyl | C35 H48 N4 O4 S | 620.8 | 621.4 |
| 81 | piperidin-1-yl-4-phenoxy | NH-ethyl-N-pyrrolidinyl | NH-pentyl | benzyl | C36 H48 N4 O4 S | 632.9 | 633.4 |
| 82 | piperidin-1-yl-4-phenyl | N(ethyl)-ethyl-N(CH$_3$)$_2$ | N(ethyl)$_2$ | 2,4-F$_2$-benzyl | C35 H46 F2 N4 O3 S | 640.8 | 641.4 |
| 83 | piperidin-1-yl-4-phenyl | NH-ethyl-N-pyrrolidinyl | N(ethyl)$_2$ | 4-CH$_3$-benzyl | C36 H48 N4 O3 S | 616.9 | 617.4 |
| 84 | piperidin-1-yl-4-phenyl | NH-ethyl-N-pyrrolidinyl | N(ethyl)$_2$ | 3-OCH$_3$-benzyl | C36 H48 N4 O4 S | 632.9 | 633.4 |
| 85 | piperidin-1-yl-4-phenyl | N(ethyl)-ethyl-N-pyrrolidinyl | N(ethyl)$_2$ | 3-OCH$_3$-benzyl | C38 H52 N4 O4 S | 660.9 | 661.5 |
| 86 | piperidin-1-yl-4-benzyl | N(ethyl)-ethyl-N-pyrrolidinyl | N(ethyl)$_2$ | 3-OCH$_3$-benzyl | C39 H54 N4 O4 S | 675.0 | 675.5 |
| 87 | piperidin-1-yl-4-phenyl | NH-propyl-N-(2-oxo-pyrrolidinyl) | N(ethyl)$_2$ | benzyl | C36 H46 N4 O4 S | 630.9 | 631.4 |
| 88 | piperidin-1-yl-4-phenyl | NH-(1-methyl-butyl)-N(ethyl)$_2$ | N(ethyl)$_2$ | benzyl | C38 H54 N4 O3 S | 646.9 | 647.5 |
| 89 | piperidin-1-yl-4-phenyl | NH-propyl-pyrrolidinyl | N(ethyl)$_2$ | benzyl | C36 H48 N4 O3 S | 616.8 | 617.4 |
| 90 | piperidin-1-yl-4-phenyl | NH-ethyl-N-pyrrolidinyl | NH(ethyl) | benzyl | C33 H42 N4 O3 S | 574.8 | 575.3 |
| 91 | piperidin-1-yl-4-phenyl | NH-ethyl-N-pyrrolidinyl | N(ethyl)$_2$ | 3-(OCF$_3$)-benzyl | C36 H45 F3 N4 O4 S | 686.9 | 687.2 |
| 92 | piperidin-1-yl-4-phenyl | NH-ethyl-N-pyrrolidinyl | N(ethyl)$_2$ | 2,4-di-F-benzyl | C35 H44 F2 N4 O3 S | 638.8 | 639.4 |
| 93 | piperidin-1-yl-4-phenyl | NH-ethyl-N-pyrrolidinyl | NH$_2$ | benzyl | C31 H38 N4 O3 S | 546.7 | 547.3 |
| 94 | piperidin-1-yl-4-phenyl | NH-ethyl-N-pyrrolidinyl | NH-butyl | benzyl | C35 H46 N4 O3 S | 602.8 | 603.3 |
| 95 | piperidin-1-yl-4-phenyl | NH-ethyl-N-pyrrolidinyl | NH-hexyl | benzyl | C37 H50 N4 O3 S | 630.9 | 631.3 |
| 96 | piperidin-1-yl-4-phenyl | N(ethyl)-ethyl-N(CH$_3$)$_2$ | N(ethyl)$_2$ | 3,5-(OMe$_2$)-benzyl | C37 H54 N4 O5 S | 666.2 | 667.[lacuna] |
| 97 | piperidin-1-yl-4-phenyl | N(ethyl)-ethyl-N(CH$_3$)$_2$ | N(ethyl)$_2$ | butyl | C32 H50 N4 O3 S | 570.8 | 571.3 |

TABLE 1-continued

Examples

Formula I $$\text{R1} \underset{\underset{\underset{X}{\overset{\|}{S}}}{\overset{O}{\underset{\|}{\parallel}}}}{\overset{\text{R2}}{\bigcirc}} \overset{O}{\underset{\text{R3}}{\parallel}}$$

| Ex. | R1 | R2 | R3 | X | Empirical formula | Molecular mass | MS (M + H⁺) |
|---|---|---|---|---|---|---|---|
| 98 | piperidin-1-yl-4-phenyl | N(ethyl)-ethyl-N-pyrrolidinyl | NH-butyl | benzyl | C37 H50 N4 O3 S | 630.9 | 631.3 |
| 99 | piperidin-1-yl-4-phenyl | N(ethyl)-ethyl-N-pyrrolidinyl | NH-hexyl | benzyl | C39 H54 N4 O3 S | 658.9 | 659.4 |
| 100 | piperidin-1-yl-4-phenyl | N(ethyl)-ethyl-N-pyrrolidinyl | NH-ethyl | benzyl | C35 H46 N4 O3 S | 602.8 | 603.2 |
| 101 | piperidin-1-yl-4-phenyl | N(ethyl)-ethyl-N-pyrrolidinyl | piperidin-1-yl-4-phenyl | benzyl | C44 H56 N4 O3 S | 718 | 719.3 |
| 102 | NH-propyl-phenyl | NH-ethyl-N-pyrrolidinyl | NH-pentyl | methyl | C28 H42 N4 O3 S | 514.7 | 515.3 |
| 103 | NH-butyl-phenyl | NH-ethyl-N-pyrrolidinyl | NH-pentyl | methyl | C29 H44 N4 O3 S | 528.8 | 529.3 |
| 104 | NH-1-ethyl-2,2(phenyl)₂ | NH-ethyl-N-pyrrolidinyl | NH-pentyl | methyl | C33 H44 N4 O3 S | 576.8 | 577.3 |
| 105 | NH-(p-t-butyl-benzyl) | NH-ethyl-N-pyrrolidinyl | NH-pentyl | methyl | C30 H46 N4 O3 S | 542.8 | 543.4 |
| 106 | piperidin-1-yl-4-phenyl | NH-ethyl-N-pyrrolidinyl | NH-ethyl | methyl | C27 H38 N4 O3 S | 498.7 | 499.3 |
| 107 | piperidin-1-yl-4-phenyl | N(ethyl)-ethyl-N(CH₃)₂ | NH-pentyl-5-hydroxy | benzyl | C36 H50 N4 O4 S | 634.9 | 635.3 |
| 108 | piperidin-1-yl-4-phenyl | N(CH₃)-ethyl-NHCH₃ | NH-pentyl | benzyl | C34 H46 N4 O3 S | 590.8 | 591.3 |
| 109 | piperidin-1-yl-4-phenyl | N(CH₃)-ethyl-N(CH₃)₂ | NH-pentyl | benzyl | C35 H48 N4 O3 S | 604.9 | 605.3 |
| 110 | piperidin-1-yl-4-phenyl | N(CH₃)-ethyl-NHCH₃ | NH-pentyl-5-OH | benzyl | C34 H46 N4 O4 S | 606.8 | 607.3 |
| 111 | piperidin-1-yl-4-phenyl | N(ethyl)-ethyl-N(CH₃)₂ | N(ethyl)₂ | benzyl-3-OCF₃ | C36 H47 F3 N4 O4 S | 688.9 | 689.2 |
| 112 | piperidin-1-yl-4-phenyl | N(ethyl)-ethyl-N(CH₃)₂ | N(ethyl)₂ | —CH₂-pyrid-3-yl | C34 H47 N5 O3 S | 605.8 | 606.3 |
| 113 | piperidin-1-yl-4-phenyl | N(ethyl)-ethyl-N(CH₃)₂ | N(ethyl)₂ | benzyl-4-CF₃ | C36 H47 F3 N4 O3 S | 672.9 | 673.3 |
| 114 | NH-butyl-phenyl | NH-ethyl-N-pyrrolidinyl | NH-ethyl | methyl | C26 H38 N4 O3 S | 486.7 | 487.3 |
| 115 | piperidin-1-yl-4-benzyl | NH-ethyl-N-pyrrolidinyl | NH-ethyl | methyl | C28 H40 N4 O3 S | 512.7 | 513.3 |
| 116 | piperidin-1-yl-4-phenyl | N(ethyl)-ethyl-N(CH₃)₂ | N(ethyl)₂ | benzyl-4-cyano | C36 H47 N5 O3 S | 629.9 | 630.3 |
| 117 | NH-1-ethyl-2,2(phenyl)₂ | N(ethyl)-ethyl-N(CH₃)₂ | N(ethyl)₂ | benzyl-4-CF₃ | C39 H47 F3 N4 O3 S | 708.9 | 709.0 |
| 118 | NH-butyl-phenyl | N(ethyl)-ethyl-N(CH₃)₂ | N(ethyl)₂ | benzyl-4-cyano | C35 H47 N5 O3 S | 617.9 | 618.3 |
| 119 | NH-butyl-phenyl | N(methyl)-ethyl-N-pyrrolidinyl | NH-pentyl | methyl | C30 H46 N4 O3 S | 542.8 | 543.3 |
| 120 | piperidin-1-yl-4-phenyl | N(methyl)-ethyl-NH-ethyl | NH-pentyl | benzyl | C35 H48 N4 O3 S | 604.9 | 605.3 |
| 121 | 1,2,3,4-tetrahydro-isoquinolin-2-yl | N(methyl)-ethyl-N-pyrrolidinyl | NH-pentyl | methyl | C29 H42 N4 O3 S | 526.7 | 527.3 |
| 122 | 1,2,3,4-tetrahydro-isoquinolin-2-yl | NH-ethyl-N-pyrrolidinyl | N(ethyl)₂ | benzyl-3-OCH₃ | C34 H44 N4 O4 S | 604.8 | 605.3 |
| 123 | piperidin-1-yl-4-benzyl | N(ethyl)-ethyl-N(CH₃)₂ | N(ethyl)₂ | benzyl-4-CH₃ | C37 H52 N4 O3 S | 632.9 | 633.4 |
| 124 | 1,2,3,4-tetrahydro-isoquinolin-2-yl | N(ethyl)-ethyl-N(CH₃)₂ | N(ethyl)₂ | benzyl-4-CH₃ | C34 H46 N4 O3 S | 590.8 | 591.5 |
| 125 | 1,2,3,4-tetrahydro-isoquinolin-2-yl | NH-ethyl-N-pyrrolidinyl | NH-propyl-OCH₃ | methyl | C27 H38 N4 O4 S | 514.7 | 515.3 |
| 126 | 1,2,3,4-tetrahydro-isoquinolin-2-yl | N(ethyl)-ethyl-N-pyrrolidinyl | N(ethyl)₂ | benzyl-3-OCH₃ | C36 H48 N4 O4 S | 632.9 | 633.6 |
| 127 | NH-1-ethyl-2,2(phenyl)₂ | NH-ethyl-N-pyrrolidinyl | NH-propyl-OCH₃ | methyl | C32 H42 N4 O4 S | 578.8 | 579.3 |
| 128 | piperidin-1-yl-4-phenyl | NH-ethyl-N-pyrrolidinyl | NH-butyl | benzyl-4-CH₃ | C36 H48 N4 O3 S | 616.9 | 617.6 |
| 129 | piperidin-1-yl-4-phenyl | N(butyl)-ethyl-N-pyrrolidinyl | NH-pentyl | methyl | C34 H52 N4 O3 S | 596.9 | 597.3 |
| 130 | piperidin-1-yl-4-phenyl | N(butyl)-ethyl-N-pyrrolidinyl | N(ethyl)₂ | methyl | C33 H50 N4 O3 S | 582.9 | 583.2 |
| 131 | piperidin-1-yl-4-phenyl | NH-propyl-N-pyrrolidinyl | N(butyl)₂ | methyl | C34 H52 N4 O3 S | 596.9 | 597.2 |
| 132 | piperidin-1-yl-4-phenyl | N(ethyl)-ethyl-N-pyrrolidinyl | N(butyl)₂ | methyl | C35 H54 N4 O3 S | 610.9 | 611.2 |
| 133 | piperidin-1-yl-4-phenyl | NH-ethyl-N-piperidinyl | NH(pentyl) | methyl | C31 H46 N4 O3 S | 554.8 | 555.3 |
| 134 | piperidin-1-yl-4-phenyl-4-NH₂ | NH-ethyl-N-pyrrolidinyl | NH-pentyl | methyl | C30 H45 N5 O3 S | 555.8 | 556.3 |
| 135 | piperidin-1-yl-4-phenyl | NH-ethyl-N-pyrrolidinyl | NH-butyl | benzyl-3,5(OCH₃)₂ | C37 H50 N4 O5 S | 662.9 | 663.6 |
| 136 | piperidin-1-yl-4-(4-NH₂-phenyl) | N(butyl)-ethyl-N-pyrrolidinyl | N(ethyl)₂ | methyl | C33 H51 N5 O3 S | 597.9 | 598.5 |
| 137 | piperidin-1-yl-4-(4-NH₂-phenyl) | N(ethyl)-ethyl-N-pyrrolidinyl | NH-butyl | methyl | C31 H47 N5 O3 S | 569.8 | 570.4 |
| 138 | piperidin-1-yl-4-phenyl | NH-ethyl-N-pyrrolidinyl | NH-hexyl | methyl | C31 H46 N4 O3 S | 554.8 | 555.4 |
| 139 | piperidin-1-yl-4-phenyl | NH-ethyl-N-pyrrolidinyl | NH-pentyl | benzyl-3-NH₂ | C36 H49 N5 O3 S | 631.9 | 632.4 |
| 140 | piperidin-1-yl-4-phenyl | N(ethyl)-ethyl-N(CH₃)₂ | NH-pentyl-NH₂ | benzyl | C36 H51 N5 O3 S | 633.9 | 634.4 |

Example 141

Methanesulfonate of Example 54

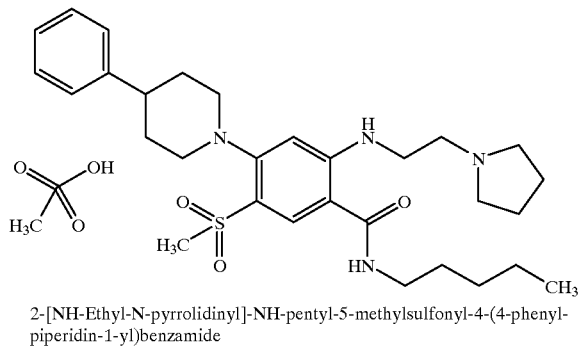

2-[NH-Ethyl-N-pyrrolidinyl]-NH-pentyl-5-methylsulfonyl-4-(4-phenyl-piperidin-1-yl)benzamide 20.0 g of the free base from Example 54 are dissolved in hot isopropanol and admixed with 5.1 ml of methanesulfonic acid. After cooling of the solution to room temperature, the resulting suspension is stirred at a temperature between 0° C. and 5° C. for a further hour, and the product is then obtained by filtration. The crude product is recrystallized from 200 ml of isopropanol and dried at 50° C. under reduced pressure. This gives 21.0 g of the salt of melting point 205° C.–208° C.

Example 142

Toluenesulfonate of Example 54

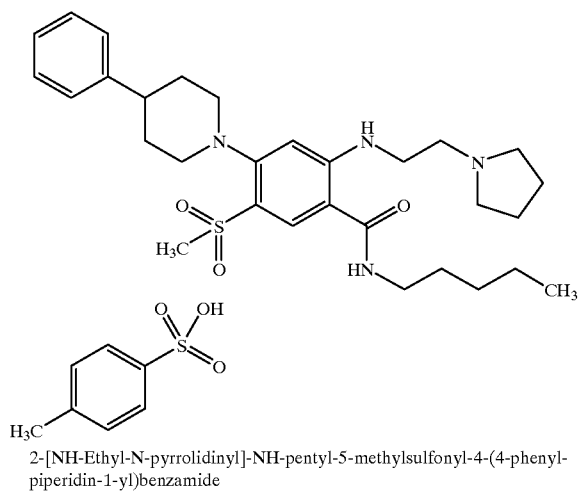

2-[NH-Ethyl-N-pyrrolidinyl]-NH-pentyl-5-methylsulfonyl-4-(4-phenyl-piperidin-1-yl)benzamide

Example 143

Maleate of Example 54

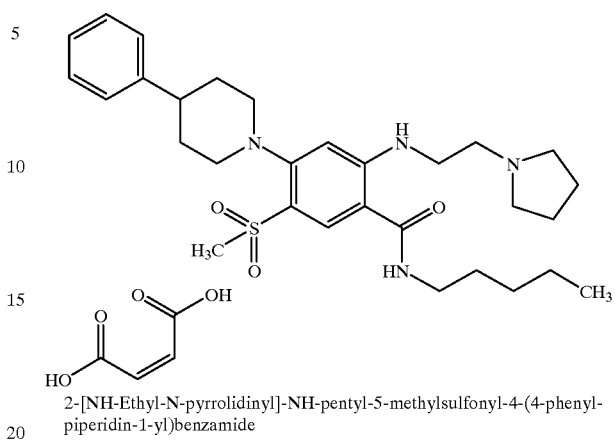

2-[NH-Ethyl-N-pyrrolidinyl]-NH-pentyl-5-methylsulfonyl-4-(4-phenyl-piperidin-1-yl)benzamide The compounds of the formula I are distinguished by beneficial effects on lipid metabolism, and they are suitable in particular as hypolipidemics. The compounds can be employed alone or in combination with other lipid-lowering agents. Such other lipid-lowering agents are mentioned, for example, in the Rote Liste, Chapter 58. The compounds are suitable for the prophylaxis and, in particular, for the treatment of hyperlipidemia.

Arteriosclerosis is a complex disorder of the metabolic and circulatory systems. Elevated plasma LDL cholesterol is one of the main risk parameters for this disorder. In humans, LDL cholesterol is mostly removed from the blood circulation via the LDL receptor in the liver. A reduction in the plasma LDL cholesterol reduces the risk of arteriosclerosis and thus also the overall mortality. The compounds according to the invention are thus also suitable for the prophylaxis and for the treatment of arteriosclerotic disorders.

The activity of the compounds was tested as follows:

1) In vitro Determination of LDL Receptor Induction Using the Luciferase Assay

LDL-receptor induction is determined using the Luciferase assay as follows: for this purpose, a regulatory DNA fragment (4 kb) of the human LDL receptor gene which contains the complete promoter region is coupled to the firefly Luciferase reporter gene and stably transfixed into a Hep-G2 cell line. Cells from this line were seeded out on collagen-coated 96-well plates in MEM (minimum essential medium). After 24 hours in culture, the test substances, dissolved in DMSO, were added in final concentrations of 10 nM to 10 $\mu$M (final DMSO concentration=2%). The substances were incubated for 12–18 hours overnight (4 wells/conc. in each case), then D-luciferin was added as substrate for the Luciferase, and the luminescence was measured. The measured luminescence as a percentage of the control (control=100%) incubated only with DMSO indicates the extent of the relative LDL-receptor induction (Table 2).

Further details of the method are described in: Current Protocols in Molecular Biology, F. M. Ausubel, R. Brent, R. E. Kingston, D. D. Moore, J. G. Seidman, J. A. Smith and Kevin Struhl editors, J. Wiley and Sons Inc., U.S.A.

TABLE 2

LDL-receptor induction by selected examples in % of the control

| Example | LDL-receptor induction (% of control); concentration of the test compound in μM in ( ) |
|---|---|
| 2 | 225% (1.5 μM) |
| 3 | 276% (1.5 μM) |
| 4 | 190% (0.15 μM) |
| 9 | 170% (0.15 μM) |
| 14 | 176% (1.5 μM) |
| 22 | 224% (0.15 μM) |
| 25 | 346% (1.5 μM); 152% (0.05 μM) |
| 30 | 255% (1.5 μM); 199% (0.15 μM) |
| 34 | 291% (4 μM); 210% (0.15 μM) |
| 37 | 227% (1.5 μM); 204% (0.15 μM) |
| 39 | 185% (0.15 μM) |
| 42 | 149% (0.05 μM) |
| 53 | 221% (0.15 μM); 197% (0.05 μM) |
| 54 | 223% (0.15 μM) |
| 57 | 222% (0.15 μM) |
| 62 | 205% (0.05 μM) |
| 67 | 203% (0.15 μM) |
| 76 | 244% (0.15 μM) |
| 78 | 200% (0.15 μM) |
| 80 | 239% (0.15 μM) |
| 82 | 227% (0.15 μM) |
| 83 | 212% (0.15 μM) |
| 84 | 240% (0.05 μM) |
| 91 | 231% (0.05 μM) |
| 96 | 196% (0.05 μM) |
| 105 | 236% (0.05 μM) |
| 107 | 288% (0.05 μM) |
| 113 | 217% (0.05 μM) |
| 116 | 235% (0.05 μM) |
| 141 | 280% (0.15 μM) |
| 142 | 281% (0.15 μM) |
| 143 | 308% (0.15 μM) |

2) In vivo Determination of Reduction in LDL Cholesterol in Hamsters

Cholesterol-lowering effect of LDL-receptor inducers in hyperlipemic hamsters

In this animal experiment, the effect of LDL-receptor inducers after bolus administration to hamsters on a lipid-rich diet was investigated.

The test animals used were male Syrian hamsters (Charles River) with an average body weight of 100–120 g at the start of adaptation. The animals were divided into groups (n=6) on the basis of body weight. Severe hyperlipidemia was induced by feeding with a diet supplemented with 15% butter and 3% cholesterol. The treatment started after preliminary feeding for 2 weeks. The test substances were administered orally by gavage once a day over a period of 10 days. The plasma lipid level was analyzed after 10 days.

Table 3 shows the relative changes in the lipid level in % compared with placebo-treated control animals.

TABLE 3

Relative change in the plasma lipid level in hyperlipidemic hamsters after oral treatment for 10 days [%].

| Group | Treatment (Ex. No./Dose) | Total cholesterol | LDL cholesterol | Triglycerides |
|---|---|---|---|---|
| 1 | Control I | — | — | — |
| 2 | 37 20 mg/kg p.o. | −21 | −31 | −46 |
| 3 | 53 10 mg/kg p.o. | −7 | −52 | +21 |
| 4 | 53 20 mg/kg p.o. | −16 | −57 | −11 |
| 5 | 53 40 mg/kg p.o. | −17 | −58 | −23 |

The good lipid-lowering effect of the compounds according to the invention is evident from the marked reduction in total cholesterol, LDL cholesterol and triglycerides.

A comparative test was carried out by the Luciferase assay described above using 2,4-dichloro-5-(3,5-dimethylpiperidinosulfamoyl)benzoic acid and the compound from Example 42.

Example 42

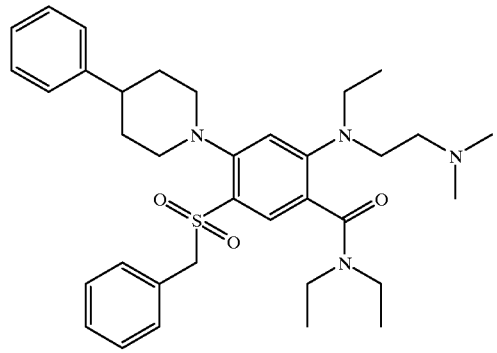

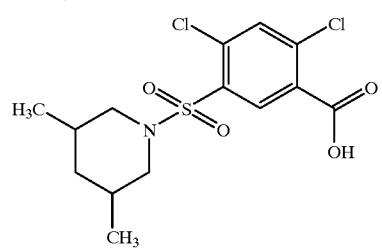

2,4-Dichloro-5-(3,5-dimethylpiperidinosulfamoyl) benzoic acid

Luciferase Assay

| Substance | 4 μM | 1.5 μM | 0.15 μM | 0.05 μM |
|---|---|---|---|---|
| | LDL-receptor induction in %, compared with control | | | |
| Example 42 | 278 | 250 | 219 | 204 |
| 2,4-Dichloro-5-(3,5-dimethyl-piperidinosulfamoyl)benzoic acid | 100 | 90 | 90 | 94 |

Thus, the compounds of the formula I according to the invention exhibit considerably improved activity compared with 2,4-dichloro-5-(3,5-dimethylpiperidinosulfamoyl) benzoic acid.

For detailed illustration of the preparation, one example (No. 42) is described precisely below.

Example

2-[(2-Dimethylaminoethyl)ethylamino]-N,N-diethyl-5-phenylmethane-sulfonyl-4-(4-phenylpiperidin-1-yl)benzamide (Table 1, Example 42)

1. Preparation of 3-chlorosulfonyl-4-chloro-6-fluorobenzoic acid

At 20° C., 20 g (0.115 mol) of 4-chloro-2-fluorobenzoic acid are added a little at a time with stirring to 100 ml of chlorosulfonic acid. The reaction mixture is heated with stirring at 120° C. for 5 hours. For work-up, the cold reaction mixture is introduced dropwise with vigorous stirring into 5 l of an ice/water mixture. The resulting precipitate is filtered off with suction, washed with water and then dried in a vacuum drying cabinet at 50° C. for 1 hour.

This gives 61.5 g of 3-chlorosulfonyl-4-chloro-6-fluorobenzoic acid, colorless crystals of melting point 135° C.

2. Preparation of 5-carboxy-2-chloro-4-fluorobenzosulfinic acid disodium salt 71 g (0.563 mol; 2.5 equivalents) of sodium sulfite are dissolved in 200 ml of water and, with ice-cooling, admixed with 61.5 g of the compound from procedure 1. (3-chlorosulfonyl-4-chloro-6-fluorobenzoic acid). By adding conc. aqueous sodium hydroxide solution, the pH of the solution is adjusted to pH 9, and the solution is stirred at 20° C. for 6 hours. Using conc. aqueous hydrochloric acid, the solution is then acidified to pH 1, resulting in the precipitation of the sulfinic acid formed. The sulfinic acid is filtered off, the reaction product is dissolved in 600 ml of water and the pH of the solution is adjusted to pH 10 by addition of conc. aqueous NaOH. The mixture is filtered through activated carbon, the solvent is removed under reduced pressure and the oily residue is then crystallized by addition of 100 ml of acetone.

This gives 59.2 g of colorless crystals (93% of theory) which are directly reacted further.

3. Preparation of benzyl 4-chloro-2-fluoro-5-phenylmethanesulfonyl-benzoate 28.3 g (0.1 mol) of the compound prepared under 2. are suspended in 250 ml of N-methyl-2-pyrrolidone and admixed successively with 41 g (0.24 mol) of benzyl bromide and 4.6 g (0.3 mol) of potassium carbonate. The reaction mixture is stirred at 60° C. for 8 hours. For work-up, the reaction mixture is, after cooling to room temperature, added to 1.5 liter of ice water, resulting, after 20 minutes, in the precipitation of the reaction product in the form of a colorless solid which is filtered off.

This gives 38.9 g (93% of theory) of benzyl 4-chloro-2-fluoro-5-phenylmethanesulfonylbenzoate; the compound is directly reacted according to 4., without further purification steps.

4. Preparation of 4-chloro-2-fluoro-5-phenylmethanesulfonylbenzoic acid 1.26 g (1.2 equivalents) of NaOH pellets are dissolved in 40 ml of water and admixed with 11 g (26.3 mmol) of benzyl 4-chloro-2-fluoro-5-phenylmethanesulfonylbenzoate, dissolved in 40 ml of tetrahydrofuran. The reaction solution is stirred at 20° C. for 3 hours.

For work-up the solution is then poured into 1 l of an ice/water mixture and the pH is adjusted to 1.2 by adding conc. aqueous hydrochloric acid. After some time, the reaction product precipitates in the form of colorless crystals. 8.4 g (97.7% of theory) of melting point 180–184° C. are obtained.

5. Preparation of 4-chloro-N,N-diethyl-2-fluoro-5-phenylmethanesulfonyl-benzamide 6.6 g (20 mmol) of the carboxylic acid from Example 4. are suspended in 50 ml of thionyl chloride and the mixture is, with stirring, heated at reflux for 1 hour. The mixture is then concentrated under reduced pressure using a rotary evaporator, and the oily residue is dissolved in 100 ml of absolute dichloromethane and, at −10° C., admixed dropwise with 3.1 g (2.1 equivalents) of diethylamine. After the addition has ended, stirring at 20° C. is continued for 1 hour. The reaction mixture is then repeatedly washed successively with saturated aqueous bicarbonate solution and water and dried using sodium sulfate, and the solvent is removed under reduced pressure using a rotary evaporator. The resulting crude product is purified by silica gel chromatography (particle size 40–63μ, from Merck Darmstadt) using n-heptane/ethyl acetate 1:1 as mobile phase ($R_F$=0.52).

Removal of the mobile phase under reduced pressure using a rotary evaporator gives 7.7 g of 4-chloro-N,N-diethyl-2-fluoro-5-phenyl-methanesulfonylbenzamide (yield quantitative).

6. Preparation of 4-chloro-2-[(2-dimethylaminoethyl)ethylamino]-N,N-diethyl-5-phenylmethanesulfonylbenzamide 5.7 g (15 mmol) of 4-chloro-N,N-diethyl-2-fluoro-5-phenylmethanesulfonyl-benzamide are dissolved in 50 ml of ethanol and, after addition of 2.6 g (22.5 mmol; 1.5 equivalents) of N,N-dimethylethylenediamine, heated at reflux for 18 hours. The solvent is then removed under reduced pressure and the residue is taken up in 100 ml of dichloromethane and washed with saturated aqueous bicarbonate solution, followed by repeated extraction with in each case 30 ml of water. The organic phase is then dried over sodium sulfate and the solvent is removed under reduced pressure using a rotary evaporator.

This gives 7.3 g of a pale yellow oil which is directly converted into the final product of the reaction sequence (see procedure 7.).

7. Preparaiton of 2-[(2-dimethylaminoethyl)ethylamino]-N,N-diethyl-5-phenylmethanesulfonyl-4-(4-phenylpiperidin-1-yl)benzamide (Ex. 42)

3.5 g (7.3 mmol) of 4-chloro-2-[(2-dimethylaminoethyl)ethylamino]-N,N-diethyl-5-phenylmethanesulfonylbenzamide from procedure 6. are mixed with 5.9 g of 4-phenylpiperidine (5 equivalents), prepared by hydrogenation of commercial 4-phenyl-1,2,3,6-tetrahydropyridine, and the mixture is stirred at 150° C. for 5 hours. The mixture is then dissolved in 150 ml of dichloromethane and extracted with saturated aqueous sodium bicarbonate solution and water. The organic phase is dried over sodium sulfate and the solvent is then removed under reduced pressure using a rotary evaporator. The crude product is purified by chromatography on silica gel (particle size 40–63μ from Merck Darmstadt) as stationary phase, using ethyl acetate/methanol, mixing ratio 2:1.

This gives 4.5 g of 2-[(2-dimethylaminoethyl)ethylamino]-N,N-diethyl-5-phenylmethanesulfonyl-4-(4-phenylpiperidin-1-yl)benzamide, pale yellow oil.

MS: C35 H48 N4 O3 S (604.9); mass spectrum 605.3 (M+H$^+$).

We claim:

1. A compound of the formula I

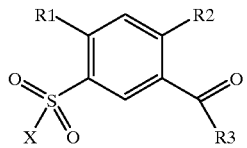

in which

X, R1, R2, R3 are, independently of one another, NR6R7, CH$_2$-pyridyl, or (CH$_2$)$_n$-phenyl, where n can be 0–6 and the phenyl radical can be substituted up to two times by F, Cl, Br, CF$_3$, NH$_2$, CN, OCF$_3$, O—(C$_1$–C$_6$)-alkyl, S—(C$_1$–C$_6$)-alkyl, (C$_1$–C$_6$)-alkyl, (C$_3$–C$_6$)-cycloalkyl, COO(C$_1$–C$_6$)-alkyl, COO(C$_3$–C$_6$)-cycloalkyl, CONH$_2$, CONH(C$_1$–C$_6$)alkyl, or CON[(C$_1$–C$_6$)alkyl]$_2$;

(C$_1$–C$_8$)-alkyl, pyrrolidinyl, piperidinyl, piperazinyl, 2-oxopiperazinyl, morpholinyl, tetrahydropyridinyl, tetrahydroquinolinyl, or tetrahydroisoquinolinyl, wherein each of the rings may be unsubstituted or substituted by phenyl, (C$_1$–C$_6$)-alkyl-phenyl, —OH, (C$_1$–C$_8$)-alkyl, (C$_1$–C$_6$)-alkyl-OH, O-phenyl, S-phenyl, (CO)—(C$_1$–C$_6$)-alkyl, or (CO)-phenyl, where the phenyl substituent is unsubstituted or substituted up to two times by F, Cl, Br, OH, CF$_3$, CN, OCF$_3$, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, (C$_1$–C$_6$)-alkyl, (C$_3$–C$_6$)-cycloalkyl, COOH, COO(C$_1$–C$_6$)alkyl, COO(C$_3$–C$_6$)cycloalkyl, CONH$_2$, CONH(C$_1$–C$_6$)alkyl, CON[(C$_1$–C$_6$)alkyl]$_2$, CONH(C$_3$–C$_6$)cycloalkyl, NH$_2$, NH—CO—(C$_1$–C$_6$)-alkyl, or NH—CO-phenyl;

R6 and R7 are, independently of one another, H, (C$_1$–C$_6$)-alkyl, (C$_1$–C$_6$)-alkyl-O—(C$_1$–C$_6$)-alkyl, O—(C$_1$–C$_6$)-alkyl, (C$_3$–C$_6$)-cycloalkyl, CO—(C$_1$–C$_6$)-alkyl, (C$_1$–C$_6$)-alkyl-NH—C(O)—(C$_1$–C$_6$)-alkyl, (C$_1$–C$_6$)-alkyl-NH—(C$_1$–C$_6$)-alkyl, (C$_1$–C$_6$)-alkyl-N—[(C$_1$–C$_6$)-alkyl]$_2$, (C$_1$–C$_6$)-alkyl-O-phenyl, CHO, CO-phenyl, or (CH$_2$)$_n$—Ar, where n can be 0–6, and Ar can be equal to phenyl, biphenylyl, 1- or 2-naphthyl, 1- or 2-tetrahydrofuranyl, 2-, 3- or 4-pyridyl, 2- or 3-thienyl, 2- or 3-furyl, 2-, 4- or 5-thiazolyl, 2-, 4- or 5-oxazolyl, 1-pyrazolyl, 3-, 4- or 5-isoxazolyl, (C$_3$–C$_6$)-cycloalkyl, piperidinyl, pyrrolidinyl, oxopyridyl, 2- or 3-pyrrolyl, 2- or 3-pyridazinyl, 2-, 4- or 5-pyrimidinyl, 2-pyrazinyl, 2-(1,3,5-triazinyl), 2-, 3- or 4-morpholinyl, 2- or 5-benzimidazolyl, 2-benzothiazolyl, 1,2,4-triazol-3-yl, 1,2,4-triazol-5-yl, tetrazol-5-yl, indol-3-yl, indol-5-yl or N-methylimidazol-2-, -4- or -5-yl and Ar can be substituted up to two times by F, Cl, Br, OH, CF$_3$, NO$_2$, CN, OCF$_3$, O—CH$_2$—O, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, (C$_1$–C$_6$)-alkyl, (C$_3$–C$_6$)-cycloalkyl, COOH, COO(C$_1$–C$_6$)alkyl, COO(C$_3$–C$_6$)cycloalkyl, CONH$_2$, CONH(C$_1$–C$_6$)alkyl, CON[(C$_1$–C$_6$)alkyl]$_2$, CONH(C$_3$–C$_6$)cycloalkyl, NH$_2$, NH—CO—(C$_1$–C$_6$)-alkyl, NH—CO-phenyl, pyrrolidin-1-yl, morpholin-1-yl, piperidin-1-yl, piperazin-1-yl, 4-methylpiperazin-1-yl, (CH$_2$)$_n$-phenyl, O—(CH$_2$)$_n$-phenyl, S—(CH$_2$)$_n$-phenyl, or SO$_2$—(CH$_2$)$_n$-phenyl, where n=0–3;

or a physiologically acceptable salt thereof.

2. A compound of claim 1, wherein

R1, R2 are, independently of one another, NR6R7, pyrrolidinyl, piperidinyl, piperazinyl, or tetrahydropyridyl, wherein each of the rings may be unsubstituted or substituted by phenyl, (C$_1$–C$_6$)-alkyl-phenyl, (C$_1$–C$_6$)-alkyl, (C$_1$–C$_6$)-alkyl-OH, O-phenyl, S-phenyl, (CO)—(C$_1$–C$_6$)-alkyl, or (CO)-phenyl, where the phenyl substituent is unsubstituted or substituted up to two times by F, Cl, Br, CF$_3$, CN, OCF$_3$, O—(C$_1$–C$_6$)-alkyl, S—(C$_1$–C$_6$)-alkyl, (C$_1$–C$_6$)-alkyl, (C$_3$–C$_6$)-cycloalkyl, COOH, COO(C$_1$–C$_6$)-alkyl, COO(C$_3$–C$_6$)cycloalkyl, CONH$_2$, CONH(C$_1$–C$_6$)alkyl, CON[(C$_1$–C$_6$)alkyl]$_2$, NH$_2$, NH—CO—(C$_1$–C$_6$)-alkyl, or NH—CO-phenyl;

R6, R7 are, independently of one another, H, (C$_1$–C$_6$)-alkyl, (C$_1$–C$_6$)-alkyl-O—(C$_1$–C$_6$)-alkyl, (C$_3$–C$_6$)-cycloalkyl, CO—(C$_1$–C$_6$)-alkyl, (C$_1$–C$_6$)-alkyl-NH—C(O)—(C$_1$–C$_6$)-alkyl, (C$_1$–C$_6$)-alkyl-NH—(C$_1$–C$_6$)-alkyl, (C$_1$–C$_6$)-alkyl-N—[(C$_1$–C$_6$)-alkyl]$_2$, or (CH$_2$)$_n$—Ar, where n can be 0–6 and Ar can be equal to phenyl, biphenylyl, 1- or 2-naphthyl, 2-, 3- or 4-pyridyl, 2- or 3-thienyl, 2-, 4- or 5-thiazolyl, 2-, 4- or 5-oxazolyl, 3- or 5-isoxazolyl, (C$_3$–C$_6$)-cycloalkyl, piperidinyl, pyrrolidinyl, 2-, 4- or 5-pyrimidinyl, 2-, 3- or 4-morpholinyl, 2- or 5-benzimidazolyl, 2-benzothiazolyl, indol-3-yl, or indol-5-yl and Ar can be substituted up to two times by F, Cl, Br, OH, CF$_3$, NO$_2$, CN, OCF$_3$, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, (C$_1$–C$_6$)-alkyl, (C$_3$–C$_6$)-cycloalkyl, COOH, COO(C$_1$–C$_6$)alkyl, COO(C$_3$–C$_6$)cycloalkyl, CONH$_2$, CONH(C$_1$–C$_6$)alkyl, NH$_2$, NH—CO-phenyl, (CH$_2$)$_n$-phenyl, O—(CH$_2$)$_n$-phenyl, or S—(CH$_2$)$_n$-phenyl, where n=0–3;

X, R3 are, independently of one another, NR8R9, pyrrolidinyl, piperidinyl, morpholinyl, (C$_1$–C$_8$)-alkyl, (CH$_2$)$_n$-phenyl, where n can be 0–6 and the phenyl radical can be substituted up to two times by F, Cl, Br, CF$_3$, CN, OCF$_3$, O—(C$_1$–C$_6$)-alkyl, S—(C$_1$–C$_6$)-alkyl, (C$_1$–C$_6$)-alkyl, (C$_3$–C$_6$)-cycloalkyl, COO(C$_1$–C$_6$)-alkyl, COO(C$_3$–C$_6$)cycloalkyl, CONH$_2$, CONH(C$_1$–C$_6$)alkyl, or CON[(C$_1$–C$_6$)alkyl]$_2$; and R8, R9 are, independently of one another, H, (C$_1$–C$_6$)-alkyl, (C$_3$–C$_6$)-cycloalkyl, CO—(C$_1$–C$_6$)-alkyl, (C$_1$–C$_6$)-alkyl-CO—(C$_1$–C$_6$)-alkyl, SO$_2$-benzyl, SO$_2$-benzyl-OCH$_3$, or (CH$_2$)$_n$—Ar, where n can be 0–6 and Ar can be equal to phenyl or thienyl and Ar can be substituted up to two times by F, Cl, Br, CF$_3$, NO$_2$, CN, OCF$_3$, O—CH$_2$—O, O—(C$_1$–C$_6$)-alkyl, S—(C$_1$–C$_6$)-alkyl, SO—(C$_1$–C$_6$)-alkyl, SO$_2$—(C$_1$–C$_6$)-alkyl, (C$_1$–C$_6$)-alkyl, (C$_3$–C$_6$)-cycloalkyl, NH—CO-phenyl, (CH$_2$)$_n$-phenyl, O—(CH$_2$)$_n$-phenyl, S—(CH$_2$)$_n$-phenyl, or SO$_2$—(CH$_2$)$_n$-phenyl, where n=0–2.

3. A compound of claim 1, wherein

R1, R2 are, independently of one another, NR6R7, piperidinyl, piperazinyl, or tetrahydropyridyl, wherein each of the rings may be unsubstituted or substituted by phenyl, (C$_1$–C$_6$)-alkyl-phenyl, (C$_1$–C$_6$)-alkyl, or (CO)—(C$_1$–C$_6$)-alkyl;

R6, R7 are, independently of one another, H, (C$_1$–C$_6$)-alkyl, (C$_1$–C$_6$)-alkyl-NH—(C$_1$–C$_6$)-alkyl, (C$_1$–C$_6$)-alkyl-N—[(C$_1$–C$_6$)-alkyl]$_2$, or (CH$_2$)$_n$—Ar, where n can be 0–6 and Ar can be equal to phenyl, 2-, 3- or 4-pyridyl, piperidinyl, pyrrolidinyl, 2-, 4- or 5-pyrimidinyl, or 2-, 3- or 4-morpholinyl and Ar can be substituted up to two times by F, Cl, Br, OH, $CF_3$, $NO_2$, CN, $OCF_3$, O—($C_1$–$C_6$)-alkyl, ($C_1$–$C_6$)-alkyl, COOH, $NH_2$, or $(CH_2)_n$-phenyl, where n can be 0–3;

X is NR8R9, piperazinyl, ($C_1$–$C_6$)-alkyl, or $(CH_2)_n$-phenyl, where n can be 0–6;

R3 is NR10R11, or piperazinyl;

R8, R9 are, independently of one another, H, ($C_1$–$C_6$)-alkyl, ($C_3$–$C_6$)-cycloalkyl, CO—($C_1$–$C_6$)-alkyl, ($C_1$–$C_6$)-alkyl-CO—($C_1$–$C_6$)-alkyl, $SO_2$-benzyl, $SO_2$-benzyl-$OCH_3$, or $(CH_2)_n$—Ar, where n can be 0–6 and Ar can be equal to phenyl or thienyl; and R10, R11 are, independently of one another, H, ($C_1$–$C_6$)-alkyl, ($C_3$–$C_6$)-cycloalkyl, CO—($C_1$–$C_6$)-alkyl, ($C_1$–$C_6$)-alkyl-CO—($C_1$–$C_6$)-alkyl, $SO_2$-benzyl, $SO_2$-benzyl-$OCH_3$, or $(CH_2)_n$—Ar, where n can be 0–6 and Ar can be equal to phenyl or thienyl.

4. A compound of claim 1, wherein

R1, R2 are, independently of one another, NR6R7, piperidinyl, piperazinyl, or tetrahydropyridyl, wherein each of the rings may be unsubstituted or substituted by phenyl, ($C_1$–$C_6$)-alkyl-phenyl, ($C_1$–$C_6$)-alkyl, or (CO)—($C_1$–$C_6$)-alkyl;

R6, R7 are, independently of one another, H, ($C_1$–$C_6$)-alkyl, ($C_1$–$C_6$)-alkyl-NH—($C_1$–$C_6$)-alkyl, ($C_1$–$C_6$)-alkyl-N—[($C_1$–$C_6$)-alkyl]$_2$, or $(CH_2)_n$—Ar, where n can be 0–6 and Ar can be equal to phenyl, 2-, 3- or 4-pyridyl, piperidinyl, pyrrolidinyl, 2-, 4- or 5-pyrimidinyl, or 2-, 3- or 4-morpholinyl and Ar can be substituted up to two times by F, Cl, Br, OH, $CF_3$, $NO_2$, CN, $OCF_3$, O—($C_1$–$C_6$)-alkyl, ($C_1$–$C_6$)-alkyl, COOH, $NH_2$, or $(CH_2)_n$-phenyl, where n can be 0–3;

X is ($C_1$–$C_6$)-alkyl or $(CH_2)_n$-phenyl, where n can be 0–6;

R3 is NR10R11 or piperazinyl; and

R10, R11 are, independently of one another, H, ($C_1$–$C_6$)-alkyl, ($C_3$–$C_6$)-cycloalkyl, CO—($C_1$–$C_6$)-alkyl, ($C_1$–$C_6$)-alkyl-CO—($C_1$–$C_6$)-alkyl, $SO_2$-benzyl, $SO_2$-benzyl-$OCH_3$, or $(CH_2)_n$—Ar, where n can be 0–6 and Ar can be equal to phenyl or thienyl.

5. A pharmaceutical composition, comprising one or more compounds of claim 1 and a pharmaceutically acceptable carrier.

6. A method of treating hyperlipidemia, comprising administering an effective amount of one or more compounds of claim 1 to a mammal in need of said treatment.

7. A method of treating arteriosclerosis, comprising administering an effective amount of one or more compounds of claim 1 to a mammal in need of said treatment.

8. A process for preparing a pharmaceutical composition having one or more compounds of claim 1, which comprises mixing at least one compound of claim 1 with a pharmaceutically acceptable excipient and bringing this mixture into a form suitable for administration.

9. A pharmaceutical composition for treating arteriosclerosis, which comprises an effective amount of a compound of claim 1 together with a pharmaceutically acceptable carrier.

10. A process for preparing a compound of claim 1, which comprises reacting, according to the reaction scheme below,

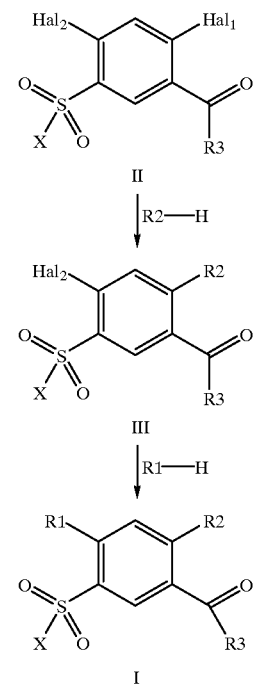

a compound of the formula II, in which X and R3 are as defined under formula I and Hal1 and Hal2 are each a halogen atom, with a compound R2—H in which R2 is as defined under formula I to give a compound of the formula III and reacting this compound with a compound R1—H in which R1 is as defined under formula I to give a compound of the formula I and reacting this compound, if appropriate, with an acid to give a pharmacologically acceptable salt thereof.

11. A method for the prophylaxis of arteriosclerosis, comprising administering an effective amount of one or more compounds of claim 1 to a mammal in need of the prophylaxis.

12. A method for the prophylaxis of a lipid metabolism disorder, comprising administering an effective amount of one or more compounds of claim 1 to a mammal in need of the prophylaxis.

* * * * *